United States Patent [19]

Khcheyan et al.

[11] 4,031,128

[45] June 21, 1977

[54] METHOD OF PREPARING ACRYLONITRILE

[76] Inventors: Khachik Egorovich Khcheyan, Volokolamskoe shosse, 1, kv. 55; Olga Mikhailovna Revenko, B. Pirogovskaya ulitsa, 29/31, kv. 107; Alla Nikolaevna Shatalova, Fortunatovskaya ulitsa, 27, kv. 1; Eleonora Grigorievna Gelperina, Schelkovskoe shosse, 44, korpus 1, kv. 19; Lidia Ivanovna Agrinskaya, Chertanovskaya ulitsa, 44, kv. 270; Georgy Avanesovich Muradian, Suschevsky val, 23, kv. 40, all of Moscow, U.S.S.R.

[22] Filed: Apr. 22, 1976

[21] Appl. No.: 679,498

[52] U.S. Cl. .......................................... 260/465.9
[51] Int. Cl.$^2$ .................................... C07C 120/00
[58] Field of Search ............................ 260/465.9

[56] References Cited

UNITED STATES PATENTS

| 3,449,399 | 6/1969 | Evans et al. | 260/465.9 |
| 3,472,890 | 10/1969 | Evans et al. | 260/465.9 |
| 3,751,443 | 8/1973 | Khcheian et al. | 260/465.9 |

OTHER PUBLICATIONS

C.A., 140728h, vol. 77, 1972.
C.A., 170216q, vol. 81, 1974.
C.A., 121079p, vol. 81, 1974.

Primary Examiner—Joseph Paul Brust

[57] ABSTRACT

A method of preparing acrylonitrile, which comprises reacting acetonitrile with methane at a temperature ranging from 650° to 1,000° C at a space velocity of 1,000 to 23,000 hr$^{-1}$ in the presence of oxygen or a mixture thereof with an inert gas and a catalyst such as calcium bromide, potassium chloride, potassium bromide, bismuth oxide, molybdenum oxide or a mixture of bismuth oxide and molybdenum oxide.

The method according to the present invention makes it possible to increase the selectivity and the conversion of the process thus increasing its efficiency by 1.5–2 times.

4 Claims, No Drawings

METHOD OF PREPARING ACRYLONITRILE

The present invention relates to a method of preparing acrylonitrile which is useful as a starting material in the production of synthetic fibers, acrylonitrile-butadiene-styrene resins, nitrile rubber, acrylamide and acrylic acid esters as well as for the synthesis of some novel products.

Known in the art is a method of preparing acrylonitrile by reacting acetonitrile with lower paraffin hydrocarbons at a temperature within the range of from 600° to 1,000° C, in the presence of an initiator such as oxygen or a mixture thereof with an inert gas. The process is conducted at a molar ratio between acetonitrile and a hydrocarbon such as methane of 1:0.5-20 and a concentration of oxygen of from 1 to 20 vol.% in the starting mixture and at a space velocity of 1,000 to 23,000 $hr^{-1}$.

Acetonitrile conversion is 20%. Acrylonitrile yield as calculated, based on the reacted acetonitrile is 50 to 60 wt.%, that of propionitrile is 10-20 wt.%, and prussic acid - 30 wt.% (Cf. USSR Inventor's Certificate No. 346937).

This prior art method has a disadvantage residing in a low yield of the desired product due to low conversion and process selectivity values.

It is an object of the present invention to increase the desired product yield.

This object is accomplished by using a method of preparing acrylonitrile by way of reacting acetonitrile with methane at a temperature within the range of from 650° to 1,000° C and at a space velocity of from 1,000 to 23,000 $hr^{-1}$ in the presence of an initiator, followed by isolation of the desired product. In accordance with the present invention the process is conducted in the presence of a catalyst such as potassium halide, calcium halide, bismuth oxide, molybdenum oxide or mixtures of oxides.

It is advisable, for the purpose of increasing the acrylonitrile yield, that as halides of potassium and calcium use be made of chlorides and bromides thereof as well as a mixture of bismuth and molybdenum oxides taken in the ratio of 1:1. It is preferable to use a catalyst deposited onto a carrier such as quartz, pumice, corundum, diatomite or titania. The amount of the catalyst deposited onto the carrier may be varied from 1 to 70% by weight.

The method of producing acrylonitrile according to the present invention is preferably performed in the following manner.

A gaseous mixture of acetonitrile, methane and oxygen or said gaseous mixture in combination with inert gases or water vapour is introduced into a reactor. The molar ratio between acetonitrile and methane in the starting mixture is varied from 1 to 0.5-8 and preferably from 1 to 1-5. Oxygen concentration in the starting mixture reaches 5 to 20 vol.%, preferably 9 to 17 vol.%, content of water vapour in the mixture is as high as 50 vol.%. The gaseous mixture, after its introduction into the reactor, is passed through a catalyst at a temperature within the range of from 650° to 1,000° C at a space velocity of from 1,000 to 23,000 $hu^{-1}$, followed by isolation of the desired product. As the catalysts in the method of the present invention use is made of potassium chloride, calcium bromide, potassium bromide, bismuth oxide, molybdenum oxide and a mixture of the oxides. As a result of interaction of acetonitrile with methane, in addition to acrylonitrile, there are formed propionitrile and prussic acid. Acetonitrile conversion reaches 50%. The yield of acrylonitrile, as calculated based on the reacted acetonitrile, is 90-100 wt.%; that of propionitrile — 5 to 20 wt.%, and that of prussic acid — 5 to 30 wt.%. The use of these catalysts makes it possible to increase the product efficiency by 1.5 to 2 times and to reduce the yield of a by-product, i.e. prussic acid.

Total yield of acrylonitrile and propionitrile as calculated based on the reacted acetonitrile is 110 to 120 wt.%. Propionitrile is readily dehydrated to acrylonitrile and may be recycled back to the apparatus thus serving as the starting material for the production of acrylonitrile.

For a better understanding of the present invention some specific Examples illustrating the method of producing acrylonitrile are given hereinbelow.

EXAMPLE 1

A gas-vapour mixture of acetonitrile, methane, oxygen and water in the molar ratio of 1;2:0.65:2.4 (oxygen content in the mixture is 12 vol.%) is passed through a catalyst, i.e. wt.% of potassium bromide on quartz. The process is performed in a quartz reactor. The space velocity of the process if 7,680 $hr^{-1}$ temperature is 800° C.

The yield of acrylonitrile as calculated based on acetonitrile is 68.0% by weight; that of propionitrile is 13.8% by weight; that of prussic acid is 24.4% by weight. Acetonitrile conversion is 31.0%.

EXAMPLE 2

A gas-vapour mixture of acetonitrile, methane, oxygen and water in the molar ratio of 1:1.25:0.314:0.53 (oxygen content in the mixture is 11 vol.%) is passed through a catalyst, i.e. 1% of potassium bromide on quartz at a space velocity of 6,050 $hr^{-1}$ at the temperature ofl 790° C. The yield as calculated based on the reacted acetonitrile, is acrylonitrile - 76.0% by weight; propionitrile 8.85% by weight; prussic acid 22.8% by weight. Acetonitrile conversion is 25.2%.

EXAMPLE 3

A gas-vapour mixture of acetonitrile, methane and oxygen in the molar ratio of 1:0.5:0.093 (oxygen content in the mixture is 6 vol.%) is passed through a catalyst, i.e. 1% of potassium bromide on quartz at a space velocity of 7,860 $hr^{-1}$ at the temperature of 800° C. The yield as calculated based on the reacted acetonitrile is acrylonitrile 54.3% by weight; propionitrile 4.95% by weight; prussic acid - 35.6% by weight. Acetonitrile conversion is 13.15%.

EXAMPLE 4

A gas-vapour mixture of methane, oxygen and water in the molar ratio of 1:5:0.43:0.795 (oxygen content in the mixture is 12 vol.%) is passed through a catalyst, i.e. 1 wt.% of potassium bromide on quartz at the space velocity of 2,360 $hr^{-1}$ at the temperature of 800° C. The yield, as calculated based on the reacted acetonitrile is acrylonitrile 61.5% by weight; propionitrile 24.5% by weight; prussic acid 22.7% by weight. Acetonitrile conversion is 47.0%.

EXAMPLE 5

A gas-vapour mixture of acetonitrile, methane, oxygen, and water in the molar ratio of 1:4:0.33:0.725

(oxygen content in the mixture is 6 vol.%) is passed through a catalyst, i.e. 1 wt.% of potassium bromide on quartz at the space velocity of 2,140 hr$^{-1}$ at the temperature of 700° C. The yield, as calculated based on the reacted acetonitrile is acrylonitrile 84.5% by weight; propionitrile 20.05% by weight; prussic acid 15.5% by weight. Acetonitrile conversion is 17.5%.

EXAMPLE 6

A gas-vapour mixture of acetonitrile, methane, oxygen and water in the molar ratio of 1:4.2:0.82:1.08 (oxygen content in the mixture is 13 vol.%) is passed through a catalyst, i.e. 1 wt.% of potassium bromide on quartz at the space velocity of 9,850 hr$^{-1}$ at the temperature of 840° C. The yield, as calculated based on the reacted acetonitrile, is acrylonitrile 66.0% by weight; propionitrile 14.5% by weight; prussic acid 25.0% by weight. Acetonitrile conversion is 31.0%.

EXAMPLE 7

A gas-vapour mixture of acetonitrile, methane, oxygen and water in the molar ratio of 1:1.9:0.515:0.555 (oxygen content in the mixture is 14.4 vol.%) is passed through a catalyst, i.e. 1 wt.% of potassium bromide on quartz at the space velocity of 7,150 hr$^{-1}$ at the temperature of 812° C. The yield as calculated based on the reacted acetonitrile is acrylonitrile 62.5% by weight; propionitrile 9.85% by weight; prussic acid 29.1% by weight. Acetonitrile conversion is 30.7%.

EXAMPLE 8

A gas-vapour mixture of acetonitrile, methane, oxygen and water in the molar ratio of 1:3:1.22:2.8 (oxygen content in the mixture is 9 vol.%) is passed through a catalyst, i.e. 1 wt.% of potassium bromide on quartz at the space velocity of 8,450 hr$^{-1}$ at the temperature of 795° C. The yield, as calculated based on the reacted acetonitrile is acrylonitrile 64.0% by weight, propionitrile 16.8% by weight; prussic acid 25.0% by weight. Acetonitrile conversion is 29.1%.

EXAMPLE 9

A gas-vapour mixture of acetonitrile, methane, oxygen and water in the molar ratio of 1:5:0.665:0.75 (oxygen content in the mixture is 9.0 vol.%) is passed through a catalyst, i.e. 1 wt.% of potassium bromide on quartz, at the space velocity of 12,250 hr$^{-1}$ at the temperature of 840° C. The yield as calculated based on the acetonitrile is acrylonitrile 56.3% by weight; propionitrile 19.8% by weight; prussic acid 27.5% by weight. Acetonitrile conversion is 26.2%.

EXAMPLE 10

A gas-vapour mixture of acetonitrile, methane, oxygen and water in the molar ratio of 1:1.5:0.25:1.0 (oxygen content in the mixture is 10 vol.%) is passed through a catalyst i.e. 40 wt.% of potassium bromide on pumice at the space velocity of 3,500 hr$^{-1}$ at the temperature of 725° C. The yield, as calculated based on the reacted acetonitrile is acrylonitrile is 81.3% by weight; propionitrile 17.5% by weight; prussic acid 15.8% by weight. Acetonitrile conversion is 20.8%.

EXAMPLE 11

A gas-vapour mixture of acetonitrile, methane, oxygen and water in the molar ratio of 1:1.5:0.25:1 (oxygen content in the mixture is 6.6 vol.%) is passed through a catalyst, i.e. 10 wt.% of potassium bromide on corundum at the space velocity of 3,500 hr$^{-1}$ at the temperature of 725° C. The yield, as calculated based on the reacted acetonitrile is acrylonitrile 70.0% by weight; propionitrile 4.7% by weight; prussic acid 27.8% by weight. Acetonitrile conversion is 22.4%.

EXAMPLE 12

A gas-vapour mixture of acetonitrile, methane, oxygen and water in the molar ratio of 1:2.4:0.6 (oxygen content in the mixture being 10 vol.%) is passed through a catalyst, i.e. 1 wt.% of potassium bromide on quartz placed into a titanium reactor at the space velocity of 4,800 hr$^{-1}$ at the temperature of 750° C. The yield, as calculated based on the reacted acetonitrile, is acrylonitrile 65.7% by weight; propionitrile 7.8% by weight prussic acid 28.5% by weight. Acetonitrile conversion is 29.2%.

EXAMPLE 13

A gas-vapour mixture of acetonitrile, methane, oxygen and water in the molar ratio of 1:1.5:0.25:1 (oxygen content in the mixture being 6.6 vol.%) is passed through a catalyst, i.e. 2% by weight of potassium chloride on quartz at the space velocity of 3,500 hr$^{-1}$ at the temperature of 725° C. The yield, as calculated based on the reacted acetonitrile, is acrylonitrile 72.3% by weight, propionitrile 12% by weight; prussic acid 23% by weight. Acetonitrile conversion is 9.5%.

EXAMPLE 14

A gas-vapour mixture of acetonitrile, methane, oxygen and water in the molar ratio of 1:1.5:0.25:1 (oxygen content in the mixture being 10 vol.%) is passed through a catalyst, i.e. 15% by weight of potassium bromide on titania at the space velocity of 3,500 hr$^{-1}$ at the temperature of 725° C. The yield, as calculated based on the reacted acetonitrile, is acrylonitrile 100% by weight; propionitrile 20.8% by weight; prussic acid 7.6% by weight. Acetonitrile conversion is 10.0%.

EXAMPLE 15

A gas-vapour mixture of acetonitrile, methane, oxygen and water in the molar ratio of 1:1.5:0.25:1 (oxygen content in the mixture being 10 vol.%) is passed through a catalyst, i.e. 2.5% by weight of calcium bromide on quartz at the space velocity of 3,500 hr$^{-1}$ at the temperature of 725° C. The yield, as calculated based on the reacted acetonitrile, is acrylonitrile 87.2% by weight; propionitrile 15.4% by weight; prussic acid 18.5% by weight. Acetonitrile conversion is 15.7%.

EXAMPLE 16

A gas-vapour material of acetonitrile, methane, oxygen and water in the molar ratio of 1:4:1.1:0.68 (oxygen content in the mixture is 12% by volume) is passed through a catalyst, i.e. 1% by weight of potassium bromide on quartz at the space velocity of 1,000 hr$^{-1}$ and at the temperature of 725° C. The yield, as calculated based on the reacted acetonitrile, is acrylonitrile 61.5% by weight, propionitrile 24.5% by weight; prussic acid 22.6% by weight. Acetonitrile conversion is 47%.

EXAMPLE 17

A gas-vapour mixture of acetonitrile, methane, oxygen and water in the molar ratio of 1:7:2:4.95 (oxygen content in the mixture being 13.5 vol.%) is passed through a catalyst, i.e. 1 wt.% of potassium bromide on quartz at the space velocity of 23,000 hr$^{-1}$ and at the temperature of 930° C. The yield, as calculated based on the reacted acetonitrile, is acrylonitrile 88% by weight; propionitrile 9.4% by weight; prussic acid 16.5% by weight. Acetonitrile conversion is 45%.

EXAMPLE 18

A gas-vapour mixture of acetonitrile, methane, oxygen and water in the molar ratio of 1:1:0.37:0.6 (oxygen content in the mixture being 12 vol.%) is passed through a catalyst, i.e. 1 wt.% of bismuth oxide on quartz at the space velocity of 8,500 hr$^{-1}$ and at the temperature of 725° C. The yield, as calculated based on the reacted acetonitriles, is acrylonitrile 83.7% by weight; propionitrile 6.3% by weight; prussic acid 20% by weight. Acetonitrile conversion is 21.6%.

EXAMPLE 19

A gas-vapour mixture of acetonitrile, methane, oxygen and water in the molar ratio of 1:3.2:0.31:0.5 (oxygen content in the mixture being 5.2 vol.%) is passed through a catalyst, i.e. 1% by weight of bismuth oxide on quartz at the space velocity of 1,650 hr$^{-1}$ and at the temperature of 700° C. The yield, as calculated based on the reacted acetonitrile, is acrylonitrile 115°% by weight; propionitrile 5.95% by weight; prussic acid 4.4% by weight. Acetonitrile conversion is 5.0%.

EXAMPLE 20

A gas-vapour mixture of acetonitrile, methane, oxygen and water in the molar ratio of 1:4:0.9:1.8 (oxygen content in the mixture being 11.5 vol.%) is passed through a catalyst i.e. 0.8% by weight of molybdenum oxide on quartz at the space velocity of 5,600 hr$^{-1}$ and at the temperature of 720° C. The product yield, as calculated based on the reacted acetonitrile, in propionitrile 212% by weight; prussic acid 20.2% by weight; acrylonitrile 69.2% by weight. Acetonitrile conversion is 16%.

EXAMPLE 21

A gas-vapour mixture of acetonitrile, methane, oxygen and water in the molar ratio of 1:2.5:0.35:0.6 (oxygen content in the mixture being 8.2 vol.%) is passed through a catalyst, i.e. 1.5% by weight of a mixture of bismuth oxide and molybdenum oxide on quartz at the space velocity of 3,620 hr$^{-1}$ and at the temperature of 725° C. The product yield, as calculated based on the reacted acetonitrile, is acrylonitrile 107% by weight; propionitrile 3.4% by weight; prussic acid 9.7% by weight. Acetonitrile conversion is 10.0%.

EXAMPLE 22

A gas-vapour mixture of acetonitrile, methane, oxygen and water in the molar ratio of 1:5:1.05:0.7 (oxygen content in the mixture being 15.0% by volume) is passed through a catalyst, i.e. 1.5% by weight of a mixture of bismuth oxide and molybdenum oxide on quartz, at the space velocity of 8,700 hr$^{-1}$ and at the temperature of 750° C. The yield, as calculated based on the reacted acetonitrile is acrylonitrile 96.0% by weight; propionitrile 22.7% by weight; prussic acid 5.7% by weight. Acetonitrile conversion is 15.0% by weight.

EXAMPLE 23

A gas-vapour mixture is acetonitrile, methane, oxygen and water in the molar ratio of 1:3;0.7:1.5 (oxygen content in the mixture being 12.0 vol.%) is passed through a catalyst, i.e. 1.5% by weight of a mixture of bismuth oxide and molybdenum oxide on quartz at the space velocity of 10,400 hr$^{-1}$ and at the temperature of 795° C. The product yield, as calculated based on the reacted acetonitrile, is acrylonitrile 91.0% by weight; propionitrile 14.9% by weight; prussic acid 12% by weight. Acetonitrile conversion is 17.0%.

EXAMPLE 24

A gas-vapour mixture of acetonitrile, methane, oxygen and water in the molar ratio of 1:4:0.8:1.8 (oxygen content in the mixture being 11.5 vol.%) is passed through a catalyst i.e. 10% by weight of a mixture of bismuth oxide and molybdenum oxide on titania at the space velocity of 5,600 hr$^{-1}$ and at the temperature of 720° C. The product yield, as calculated based on the reacted acetonitrile, is acrylonitrile 93.0% by weight; propionitrile 9.5% by weight; prussic acid 13.0% by weight. Acetonitrile conversion is 18.0%.

EXAMPLE 25

A gas-vapour mixture of acetonitrile, methane and oxygen in the molar ratio of 1:1:0.22 (oxygen content in the mixture being 10 vol.%) is passed through a catalyst, i.e. 70% by weight of a mixture of bismuth oxide and molybdenum oxide on diatomite at the space velocity of 3,600 hr$^{-1}$ and at the temperature of 700° C. The product yield, as calculated based on the reacted acetonitrile, is acrylonitrile 87.7% by weight; propionitrile 10.7% by weight; prussic acid 15.5% by weight. Acetonitrile conversion is 19.0%.

EXAMPLE 26

A gas-vapour mixture of acetonitrile, methane and air in the molar ratio of 1:4:0.66 (oxygen content in the mixture being 8.0% by volume) is passed through a catalyst, i.e. 1.5% by weight of a mixture of bismuth oxide and molybdenum oxide on quartz, at the space velocity of 5,400 hr$^{-1}$ and at the temperature of 700° C. The product yield, as calculated based on the reacted acetonitrile, is acrylonitrile 94.0% by weight; propionitrile 12.1% by weight; prussic acid 16.2 % by weight. Acetonitrile conversion is 20.0%.

EXAMPLE 27

A gas-vapour mixture of acetonitrile, methane, oxygen and water in the molar ratio of 1:4.45:1.47:1.93 (oxygen content in the mixture being 16.7 vol.%) is passed through a catalyst, i.e. 10% by weight of bismuth oxide on quartz, at the space velocity of 7,300 hr$^{-1}$ and at the temperature of 725° C. The yield, as calculated based on the reacted acetonitrile, is acrylonitrile 91% by weight; propionitrile 13.7% by weight; prussic acid 12.5% by weight. Acetonitrile conversion is 30.3%.

EXAMPLE 28

A gas-vapour mixture of acetonitrile, methane, oxygen and water being 12.0 vol.%) is passed through a catalyst, i.e. 10% by weight of bismuth oxide on quartz, at the space velocity of 10,200 hr$^{-1}$ and at the temperature of 705° C. The product yield, as calculated based on the reacted acetonitrile, is acrylonitrile 96.5% by weight; propionitrile 14.7% by weight; prussic acid 9.2% by weight. Acetonitrile conversion is 30%.

EXAMPLE 29

A gas-vapour mixture of acetonitrile, methane, oxygen and water in the molar ratio of 1:4:0.9:1.8 (oxygen content in the mixture being 12.0 vol.%) is passed through a catalyst, i.e. a mixture of bismuth oxide and molybdenum oxide taken in the ratio of 1:1, at the space velocity of 5,760 hr$^{-1}$ and at the temperature of 750° C. The product yield, as calculated based on the reacted acetonitrile, is acrylonitrile 84.0% by weight; propionitrile 15.5% by weight; prussic acid 20.3% by weight. Converion of acetonitrile is 20.0%.

EXAMPLE 30

A gas-vapour mixture of acetonitrile, methane, oxygen and water in the molar ratio of 1:4;1:1.8 (oxygen content in the mixture being 12.8% vol.%) is passed through a reactor filled with a catalyst, i.e. bismuth oxide, at the space velocity of 5,620 hr$^{-1}$ and at the temperature of 700° C. The product yield, as calculated based on the reacted acetonitrile, is acrylonitrile 93.8% by weight; propionitrile 12.7% by weight; prussic acid 11.3% by weight. Acetonitrile conversion is 13%.

What is claimed is:

1. A method of preparing acrylonitrile comprising reacting acetonitrile with methane in a molar ratio of 1:0.5–8, at a temperature within the range of from 650 to 1,000° C at a space velocity of from 1,000 to 23,000 hr$^{-1}$ in the presence of oxygen or a mixture thereof with an inert gas and a catalyst selected from the group consisting of potassium bromide, potassium chloride, calcium bromide, bismuth oxide, molybdenum oxide and a mixture of bismuth oxide and molybdenum oxide, followed by isolation thereof.

2. A method as claimed in claim 1, wherein said mixture of bismuth oxide and molybdenum oxide is employed in the ratio of 1:1 between the oxides.

3. A method as claimed in claim 1, wherein use is made of a catalyst deposited onto a carrier selected from the group consisting of quartz, pumice, corundum, diatomite, and titania.

4. A method as claimed in claim 1 wherein the molar ratio of acetonitrile to methane is 1:1–5.

* * * * *